United States Patent [19]

Orlando et al.

[11] Patent Number: 4,460,800

[45] Date of Patent: Jul. 17, 1984

[54] PROCESS FOR PREPARATION OF HYDROXYARYLDIALKYLCARBINOLS

[75] Inventors: Charles M. Orlando, Scotia; Howard J. Klopfer, Clifton Park, both of N.Y.

[73] Assignee: General Electric Company, Schenectady, N.Y.

[21] Appl. No.: 468,094

[22] Filed: Feb. 22, 1983

[51] Int. Cl.$^3$ ............................................... C07C 39/10
[52] U.S. Cl. ..................................... 568/764; 568/811
[58] Field of Search ......................... 568/764, 811, 814

[56] References Cited

U.S. PATENT DOCUMENTS 4,239,918  12/1980  Keeley ................................ 568/640

OTHER PUBLICATIONS

"The Synthesis of N–Methyl–3–Isopropyl–4–Dimethylaminophenyl Carbamate and some Related Derivatives"; H. Gilman, S. Avakian, R. Benkeser, H. Broadbent, R. Clark, G. Karmas, F. Marshall, S. Massie, D. Shirley, and L. Woods; *J. Org. Chem.,* 19, pp. 1067,1071 (1954).

*Organic Syntheses,* Coll. vol. I, 186–187 (1941).

*Primary Examiner*—Werren B. Lone
*Attorney, Agent, or Firm*—William H. Pittman; James C. Davis, Jr.; James Magee, Jr.

[57] ABSTRACT

The preparation of hydroxyaryldialkylcarbinols by the reaction of hydroxyaryl alkyl ketones or alkyl hydroxyarenecarboxylates with Grignard reagents in a mixed ether-aromatic hydrocarbon solvent is frequently difficult on a large-scale basis because of formation of a voluminous precipitate of mixed magnesium salt. In an improvement in this process, a solution of the ketone or ester in an ether is added to the solution of the Grignard reagent.

9 Claims, No Drawings

PROCESS FOR PREPARATION OF HYDROXYARYLDIALKYLCARBINOLS

This invention relates to the preparation of hydroxyaryldialkylcarbinols and to methods therefor. In its broadest sense, the invention is an improvement in a process for the preparation of such compounds by the reaction of (A) a solution of at least one alkylmagnesium halide in a mixed ether-aromatic hydrocarbon solvent with (B) at least one hydroxyaryl alkyl ketone or alkyl hydroxyarenecarboxylate, followed by hydrolysis of the reaction mixture, said improvement comprising effecting said reaction by adding reagent A to a solution in an ether of reagent B.

Hydroxyaryldialkylcarbinols, also known as hydroxy-α,α-dialkylbenzyl alcohols, have utility in organic synthesis as intermediates for the preparation of bisphenols. For example, 3-hydroxyphenyldimethylcarbinol (m-hydroxy-α,α-dimethylbenzyl alcohol) may be reacted with phenol to yield 3,4'-isopropylidene bisphenol. The preparation of this compound is described in U.S. Pat. No. 4,239,918, and its conversion to polycarbonates and other polymers is described in U.S. Pat. No. 4,237,259; the disclosures of both of these patents are incorporated by reference herein. Other carbinols of similar structure may be used in the same way.

Hydroxyaryldialkylcarbinols may be prepared by the reaction of a hydroxyaryl alkyl ketone (hereinafter "ketone") or an aryl hydroxyarenecarboxylate (hereinafter "ester") with an alkylmagnesium halide (i.e., an alkyl Grignard reagent). This type of reaction is well known in the art. It is ordinarily effected by adding the ketone or ester to a solution of the Grignard reagent to form a mixed magnesium salt involving both the aromatic and carbinol hydroxy groups, which is then converted by hydrolysis to the hydroxyaryldialkylcarbinol. One molar proportion of the Grignard reagent reacts with the aromatic hydroxy group, yielding an alkane as by-product; therefore, at least one molar excess of the Grignard reagent (a total of two and three molar proportions in the reaction with the ketone and ester, respectively) is needed to form the desired product.

In commercial scale syntheses by this method, it is frequently necessary or desirable to use commercially available Grignard reagents which utilize mixtures of ethers and aromatic hydrocarbons as solvents. A typical such reagent is a 2 M solution of methylmagnesium chloride in a 1:1 (by weight) mixture of tetrahydrofuran and toluene. When such solutions are used on a commercial scale, the mixed magnesium salt is obtained in the form of a voluminous, agglomerated solid. Agglomeration often reaches a stage where effective agitation of the reaction mixture is difficult or impossible. This results in decreased yield, poor conversion due to entrainment of ketone or ester in the solid mass, and a substantial increase in energy expenditure.

A principal object of the present invention, therefore, is to provide an improved method for the Grignard synthesis of aryldialkylcarbinols.

Another object is to minimize problems resulting from insoluble salt formation during said synthesis.

Still another object is to improve the utilization of reactants and yield of hydroxyaryldialkylcarbinol in said Grignard reaction.

Other objects will in part be obvious and will in part appear hereinafter.

Reagent A in the process of this invention is a solution of at least one alkylmagnesium halide, typically the chloride, bromide or iodide. The alkyl group usually contains from one to about four carbon atoms and is preferably a primary alkyl group; examples are methyl, ethyl, propyl, n-butyl and isobutyl. It is most often methyl.

The solvent portion of reagent A is a mixture of at least one ether with at least one aromatic hydrocarbon. The ether may be a diether of ethylene glycol, diethylene glycol, propylene glycol or the like, or any other suitable ether; it is usually tetrahydrofuran. The aromatic hydrocarbon may be benzene, toluene or xylene and it is most often toluene. Mixtures of alkylmagnesium halides and of solvent constituents are also contemplated. The concentration of alkylmagnesium halide in the solution is usually about 0.5–3 M.

Reagent B is at least one hydroxyaryl alkyl ketone or alkyl hydroxyarenecarboxylate. The alkyl group therein usually contains from one to about four carbon atoms and is preferably methyl. The hydroxyaryl group is preferably otherwise unsubstituted, but may contain substituents which do not interfere with the Grignard reaction. Examples of suitable hydroxyaryl groups are 2-hydroxyphenyl, 3-hydroxyphenyl, 4-hydroxyphenyl, 3-hydroxy-4-nitrophenyl, 2-methoxy-3-hydroxyphenyl, 1-hydroxy-2-naphthyl and 4-hydroxy-1-naphthyl. Hydroxyphenyl groups, especially 3-hydroxyphenyl, are most preferred. Thus, the compounds most often used as reagent B are 3-hydroxyacetophenone and methyl 3-hydroxybenzoate, especcially the former.

According to the present invention, reagent A is added to a solution in an ether of reagent B. (For the purposes of this invention, reagent A is defined as including the solvent while reagent B is not.) The ether used as the solvent for reagent B is usually the same one present as a solvent constituent in reagent A, and is preferably tetrahydrofuran. However, other ethers (including those listed hereinabove) are also suitable and the ether need not be the same one present in reagent A. The solvent usually contains about 5–25% (by weight) and preferably 5–10% of reagent B.

The amount of alkylmagnesium halide present in reagent A is typically greater than the stoichiometric amount, calculated as described hereinabove. Most often, a 20–100% excess is used.

Generally, the addition of reagent A to reagent B takes place over a period from about one-half hour to about two hours. The reaction temperature is normally from about 20° to about 100° C. Most often, the addition of reagent A is effected from about 20° to about 50° C. and preferably at room temperature (i.e., about 25° C.), for reasons both of convenience and of speed and ease of reaction; and after said addition, the mixture is heated at a temperature from about 50° to about 100° C. for a period of time adequate to insure completeness of the reaction. Heating may often be conveniently effected at the reflux temperature of the solvent employed, which, in the case of tetrahydrofuran, will provide a reaction temperature from about 25° to about 70° C. The reaction is preferably carried out in an inert atmosphere such as nitrogen or helium.

The product of the above-described reaction is a mixed magnesium salt which may be converted to the hydroxyaryl dialkylcarbinol by hydrolysis. It is possible to effect hydrolysis by merely adding water, but a weakly acidic solution is preferred. Ammonium chloride solution is frequently suitable.

Following hydrolysis, the aqueous and organic layers are allowed to separate. The desired product is in the organic layer, and conventional unit operations such as washing, drying and evaporation of solvent may be employed to isolate it therefrom.

The invention is illustrated by the following examples. Example 1 illustrates the process of the invention, and Examples 2–4 are other processes included for comparison purposes.

EXAMPLE 1

To a solution of 1088 grams (8 moles) of 3-hydroxyacetophenone in 13.25 liters of tetrahydrofuran was added in a nitrogen atmosphere, over 40 minutes, a solution of 10,000 grams (20 moles) of a commercially prepared 2 M solution of methylmagnesium bromide in a mixture of equal weights of tetrahydrofuran and toluene. The mixture was stirred with a turbine stirrer during the addition. Stirring was continued as the mixture was heated under reflux (70° C.) for three hours. A solution of 5.6 liters of saturated aqueous ammonium chloride solution in 2.4 liters of water was then added and the mixture was stirred for one hour at room temperature. It was allowed to stand for one hour, the aqueous and organic layers were separated and the organic layer was washed with 7.5 liters of water, after which the tetrahydrofuran was removed by distillation. There was added 7600 ml. of a 10% aqueous solution of sodium hydroxide, and the mixture was again distilled until all tetrahydrofuran and toluene had been removed. The aqueous residue was filtered and acidified with concentrated hydrochloric acid. The precipitated solids were filtered, washed with cold water and dried to yield the desired 3-hydroxyphenyldimethylcarbinol. The yield was 976 grams, or 80% of theoretical.

EXAMPLE 2

A solution in ethyl ether of 13.6 grams (0.1 mole) of 3-hydroxyacetophenone was added over 2 hours in a nitrogen atmosphere, with stirring, to 0.34 mole of the methylmagnesium bromide solution of Example 1. During the addition, a voluminous solid precipitated; the addition had to be discontinued and the reaction mixture discarded because it completely solidified before the reaction was complete.

EXAMPLE 3

To a solution of 1150 ml. (2.3 moles) of the methylmagnesium bromide solution of Example 1 in 1200 ml. of tetrahydrofuran was added under nitrogen, with stirring, a solution of 136 grams (1 mole) of 3-hydroxyacetophenone in 500 ml. of tetrahydrofuran. The reaction temperature was maintained at 55° C. during the addition. Following the addition, the mixture was heated under reflux for 45 minutes. Hydrolysis and isolation of the product were effected as described in Example 1. There was obtained 110 grams of 3-hydroxyphenyldimethylcarbinol, or 72% of the theoretical amount.

EXAMPLE 4

To a solution of 9830 ml. (18.7 moles) of the methylmagnesium bromide solution of Example 1 and 9600 ml. of tetrahydrofuran was added a solution of 1088 grams (8 moles) of 3-hydroxyacetophenone in 2400 ml. of tetrahydrofuran. Addition was conducted under nitrogen over 40 minutes, with stirring, at a temperature of about 50° C. Voluminous precipitation of solids was noted and stirring became progressively more difficult; by the time all of the Grignard reagent had been added, the mixture was completely solid and the stirrer simply carved a hole in the solid mass, rather than effectively stirring the mixture. The mixture was heated under reflux for 4½ hours, cooled, hydrolyzed and worked up as described in Example 1. The product obtained was a tan solid, shown by high pressure liquid-liquid chromatography to be 93% 3-hydroxyphenyldimethylcarbinol and 7% unreacted 3-hydroxyacetophenone.

Example 1 above shows the effectiveness of the process of this invention for large-scale preparation of hydroxyaryldialkylcarbinols. Examples 2, 3 and 4 respectively show the ineffectiveness of the conventional method of addition (Grignard reagent to ketone) using a commercial Grignard reagent in tetrahydrofurantoluene solution, the effectiveness on a laboratory scale of a modification of that method in which the Grignard reagent is diluted with additional tetrahydrofuran, and the ineffectiveness of said modification on a larger scale. Taken together, these examples graphically demonstrate the improved processing conditions afforded by the process of this invention.

What is claimed is:

1. In a process for the preparation of a hydroxyaryldialkylcarbinol by the reaction, at a temperature from about 20° to about 100° C., of (A) a solution of at least one alkylmagnesium halide in a mixed ether-aromatic hydrocarbon solvent with (B) at least one hydroxyaryl alkyl ketone or alkyl hydroxyarenecarboxylate followed by hydrolysis of the reaction mixture, the improvement which comprises effecting said reaction by adding reagent A to a solution in an ether of reagent B.

2. A process according to claim 1 wherein a 20–100% excess of reagent A is used.

3. A process according to claim 1 for the preparation of 3-hydroxyphenyldimethylcarbinol wherein component A is a solution of at least one methylmagnesium halide and reagent B is at least one of 3-hydroxyacetophenone and methyl 3-hydroxybenzoate.

4. A process according to claim 3 wherein the methylmagnesium halide is methylmagnesium bromide.

5. A process according to claim 4 wherein reagent B is 3-hydroxyacetophenone.

6. A process according to claim 5 wherein the ether is tetrahydrofuran.

7. A process according to claim 6 wherein the aromatic hydrocarbon solvent in reagent A is toluene.

8. A process according to claim 7 wherein a 20–100% excess of reagent A is used.

9. A method according to claim 8 wherein the reaction temperature is from about 25° to about 70° C.

* * * * *